United States Patent [19]

Mays

[11] Patent Number: 4,595,629
[45] Date of Patent: Jun. 17, 1986

[54] WATER IMPERVIOUS MATERIALS

[75] Inventor: Alfred T. Mays, East Windsor, N.J.

[73] Assignee: Chicopee, New Brunswick, N.J.

[21] Appl. No.: 689,123

[22] Filed: Jan. 7, 1985

Related U.S. Application Data

[62] Division of Ser. No. 588,037, Mar. 9, 1984, Pat. No. 4,522,203.

[51] Int. Cl.[4] ............................................. B32B 27/00
[52] U.S. Cl. ................................... 428/286; 428/287; 428/296; 428/483; 428/516; 428/518; 428/520
[58] Field of Search ............... 428/375, 373, 374, 284, 428/286, 287, 296, 483, 520, 516, 518; 128/132 D, 206.19

[56] References Cited

U.S. PATENT DOCUMENTS 3,695,967 10/1972 Ross ................................. 156/306.6
4,186,235 1/1980 Bramwell .......................... 428/373

FOREIGN PATENT DOCUMENTS 1149270 4/1969 United Kingdom .

Primary Examiner—Lorraine T. Kendell
Attorney, Agent, or Firm—Leonard Kean

[57] ABSTRACT

A water impervious laminated material is described. A preferred embodiment comprises a three-layer plastic film sandwiched between and fuse bonded to two layers of conjugate fibers having a low melting sheath and a high melting core. The inner layer of the plastic film is relatively high melting while the two outer plies of the film are low melting. The sheaths of the conjugate fibers have been fuse bonded to the plastic film at a temperature below the melt temperature of the cores of the conjugate fibers so that the cores retain their initial fiber-like integrity.

5 Claims, 2 Drawing Figures

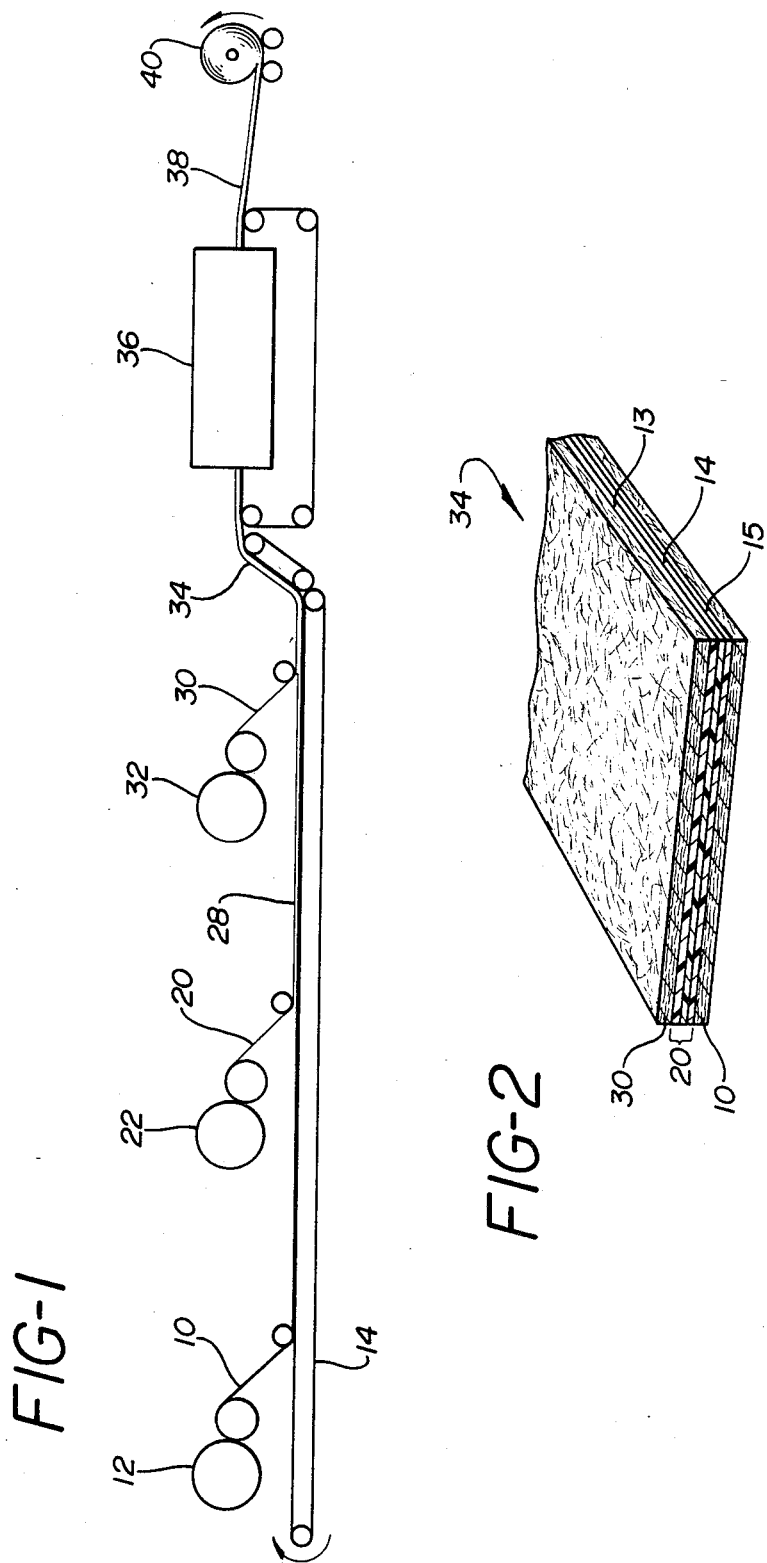

WATER IMPERVIOUS MATERIALS

This is a division of application Ser. No. 588,037, filed Mar. 9, 1984, now U.S. Pat. No. 4,522,203.

This invention relates to water impervious microfine fiber laminated materials and more particularly to absorbent disposable drapes which are impermeable to the passage of microorganisms and fluids.

BACKGROUND OF THE INVENTION

The purpose of the surgical drape is to place a bacteria barrier between the aseptic operative field and areas which are incapable of surgical cleansing. The drape also provides the physician while working on the patient, a sterile area on which to lay surgical instruments and the like. The drape should be sufficiently flexible or drapable so that it may somewhat conform to the contour of the body which it is covering, and so that it may hang down over the edges of the operating table without interfering with the physician's work. The drape should be absorbent so that it may collect exudate from the operative site and should also provide enough friction so that the drape does not slide off the patient during the operation.

Certain known disposable drapes consist of nonwoven mats of heat fusible fibers fused to one or both sides of thermoplastic sheets. However, in producing this type of fabric, the heat fusible fibers are fused so that the integrity of the fibers is destroyed. The present invention provides a multiple layer plastic film fuse bonded on at least one side to a layer of conjugate fibers having a low melting sheath and a high melting core. The sheaths of the conjugate fibers are fuse bonded to the plastic film at a temperature below the melt temperature of the cores of the conjugate fibers so that the cores retain their initial fiber-like integrity. A preferred embodiment of the present invention comprises a three-layer plastic film sandwiched between and fuse bonded to two layers of conjugate fibers. The inner layer of the plastic film is relatively high melting while the two outer layers of the film are low melting, the melt temperature of the outer layers of the film being close to the melt temperature of the fiber sheaths, so that excellent fusion takes place when these fiber sheaths and the outer layers of the film are bonded together or emboss bonded. In addition, the inner core of the three-layer plastic film is not fused during the bonding procedure and this prevents any perforations being formed in the plastic film during emboss bonding.

THE PRIOR ART

Ross in U.S. Pat. No. 3,695,967 describes a laminated material having fibrous surfaces made by laminating a nonwoven fibrous layer/thermoplastic film/nonwoven fibrous layer assembly. Lamination of the assembly is accomplished by pressing it with at least one surface which has a multiplicity of closely spaced raised areas while heating the assembly so that at least a portion of the thermoplastic film is raised to a temperature above its softening point. There is no disclosure in Ross concerning the use of conjugate fibers, and, in any event, the laminated material produced by Ross is perforated and thus would not be suitable for use as a drape which necessarily must be made impermeable to the passage of microorganisms and fluids.

A number of patents disclose the general concept of bonding a nonwoven fibrous bat to a water impervious plastic film, but in no case is there any disclosure concerning the desirability of utilizing conjugate fibers in the nonwoven bat, and thus when fuse bonding takes place between the nonwoven non-conjugate fibers and the plastic sheet, said fibers will tend to melt in the areas wherein fusion takes place and completely lose their fiber-like integrity. This has the effect of reducing the loft or low bulk density characteristics of the nonwoven bat so that the absorption capacity and strength of the bat is also reduced. Examples of patents disclosing the bonding of bats of monofilament fibers to plastic sheets are as follows: Stoller, U.S. Pat. No. 3,988,519; Portolani, U.S. Pat. No. 3,551,284 and Prentice, U.S. Pat. No. 3,676,242.

The Gore et al. U.S. Pat. No. 4,194,041 describes a waterproof laminate comprising an outer layer of a hydrophobic material and an inner layer which permits the transfer of moisture vapor. Textile layers can be added for strength and aesthetic characteristics. The textile layers are on the outside of the laminate of the textile layers and the hydrophobic and moisture-vapor permeable layers. No conjugate fibers are disclosed.

The Falcone U.S. Pat. No. 3,513,057 describes a process for bonding textile fibers to elastomeric ethylene/higher alpha-olefin copolymers. In this case, too, no conjugate fibers are disclosed.

The Hansen U.S. Pat. No. 3,809,077 discloses a surgical drape constructed of two layers of thin absorbent compacted webs of randomly interlaced staple textile fibers having disposed therebetween a thin drapable impervious sheet of a thermoplastic film which is adherently bonded to the absorbent sheets across the contacting surfaces thereof by means of a soft latex adhesive. The fuse bonding of conjugate fibers is not disclosed.

The present invention provides a soft drapable composite which is impervious to water. The use of conjugate fibers composed of higher and lower melting components, preserves the integrity of the higher melting component, in view of the fact that the fusion process is carried out below the melting temperature of the higher melting component. The preservation of the integrity of the fibers, maintains the high loft or low bulk density characteristics of the nonwoven layers in order to achieve good absorption capacity and strength. Furthermore, in accordance with a preferred embodiment of the present invention, the melt temperature of the outer layers of the plastic film is chosen so as to substantially match the melt temperature of the lower melting component of the conjugate fiber. In this manner a far stronger and more intimate bond is formed, especially in the instance wherein the same material is used for the outer layer of the plastic sheet as well as the lower melting component of the conjugate fiber.

In addition, the preferred embodiment of the present invention utilizes a plastic sheet comprising a three-layer coextruded film in which the central layer possesses a higher melt temperature than the two outer layers. It is very unlikely that the inner layer of the three-layer composite plastic film, would be punctured during emboss bonding, especially in view of the fact that said inner layer is chosen to possess a melt temperature above that at which bonding between the plastic sheet and the layers of conjugate fibers, takes place. This feature is highly important in the case of a barrier drape in which bacterial transfer must be prevented.

SUMMARY OF THE INVENTION

In accordance with the present invention there is provided a water impervious laminated material comprising at least one layer of conjugate fibers, said layer of conjugate fibers having a first face and an opposite face, the conjugate fibers being composed of a lower melting component and a higher melting component wherein a substantial proportion of the surfaces of said fibers comprises said lower melting component, said lower melting component of said conjugate fibers which lie on said first face being fuse bonded to a first layer of a plastic laminated film which comprises said first layer and at least one additional layer, said first layer of said film being thermoplastic and possessing a lower melt temperature than said additional layer of said film, said lower melting component of said fibers having been fuse bonded at a temperature below the melt temperature of said higher melting component of said fibers so that the latter component retains its initial fiber-like integrity. Preferably, the melt temperature of the lower melting component of the conjugate fibers is not more than 35° C. higher or lower than the melt temperature of the first layer of the thermoplastic film.

In accordance with a preferred embodiment of the present invention, there is provided a water impervious laminated material comprising an inner plastic film sandwiched between two layers of conjugate fibers, each of said layers of conjugate fibers having a first face and an opposite face, said conjugate fibers being composed of a lower melting component and a higher melting component, wherein a substantial proportion of the surfaces of said fibers comprises said lower melting component, said plastic film comprising a three-layer structure having an inner layer sandwiched between and bonded to two outer layers, said inner layer of said film structure having a melt temperature higher than the melt temperatures of each of said outer layers of said film structure, said lower melting components of both layers of said conjugate fibers which lie on said first faces having been fuse bonded to the adjacent outer layers of said film structure at a temperature below the melt temperature of said higher melting component of said fibers so that the latter component retains its initial fiber-like integrity.

In accordance with a further embodiment of the present invention, at least one layer of conjugate fibers is blended with non-conjugate fusible fibers, with the proviso that the first face of said layer of conjugate fibers contains a plurality of conjugate fibers in the blend. The specific nature and melt temperatures of the non-conjugate portions of the blend are not critical since the conjugate-rich material in the first face of the layer which is fused to the plastic film ensures the good bonding features provided by the present invention.

The outer layers of the film of the present invention (which constitute the lower melting layers thereof) may consist of any suitable relatively low melting thermoplastic polymer such as ethylene/propylene copolymer, polyester copolymer, low density polyethylene, ethylene/vinyl acetate copolymer, polyethylene, chloronated polyethylene, or polyvinylchloride. A preferred higher melting inner layer of the plastic film comprises isotactic polypropylene. However, a number of other higher melting thermoplastic materials such as polyester or polyamide may also be used.

Although continuous filaments of conjugate fibers may be employed in accordance with the present invention, nevertheless, the preferred conjugate fibers are textile length, that is they are fibers having lengths of from ¼ inch and preferably from ½ inch up to about 3 inches or more in length. Such conjugate fibers can be bi-component fibers such as the sheath/core or side-by-side bi-component fibers wherein there is a lower melting component and a higher melting component, with a significant proportion and preferably a major proportion of the surface of the fiber being the lower melting component. Preferably the lower melting component is a polyolefin, and most preferably polyethylene. In many cases the sheath/core bi-component fibers are preferred because they exhibit a better bonding efficiency than the side-by-side bi-component fibers, and because in some cases the side-by-side bi-component fibers may exhibit an excessive tendency to curl, crimp, or shrink during the heat bonding step. Both concentric and eccentric sheath/core bi-component fibers can be used.

The nonwoven conjugate fiber layers of the present invention can have basis weights from about 0.25 to about 3.0 ounces per square yard. The bulk density of said layers of conjugate fibers will be below about 0.1 grams per cubic centimeter, e.g., from about 0.03 to about 0.08 grams per cubic centimeter, and preferably from 0.04 to about 0.06 grams per cubic centimeter. The conjugate fiber nonwoven layers used in the present invention have a good absorbent capacity, and the excellent resistance of the nonwoven layers to wet collapse contributes to this good absorbent capacity.

In the thermal bonding step the lower melting component of the conjugate fiber is at least partially fused so that where the fused surface touches another conjugate fiber, welding or fusing together of the two fibers will occur. It is important in order to achieve the objects of this invention that the conjugate fibers remain fibers, i.e., that the higher melting component of the conjugate fiber not melt or shrink significantly and thereby become beads or the like.

In accordance with a preferred embodiment of the present invention, the inner layer of the film structure comprises isotactic polypropylene and the two outer layers comprise ethylene/vinyl acetate copolymer. The preferred conjugate fiber comprises a polyethylene/polyester sheath/core bi-component fiber. A further desirable embodiment of the film used in the present invention is one in which the inner layer comprises isotactic polypropylene and the two outer layers comprise polyethylene. Yet a further desirable embodiment of the film used in the present invention is one in which the inner layer comprises isotactic polypropylene, one of the outer layers comprises polyethylene and the other of the outer layers comprises ethylene/vinyl acetate copolymer.

The preferred three-layer film used in the present invention is preferably initially prepared by coextrusion in accordance with methods well known in the art. However, said three-layer film structure may also be prepared by laminating separate components together and thereafter said components may be heat bonded together or bonded by means of suitable adhesives.

The present invention also includes a process for preparing a water impervious laminated material comprising at least one layer of conjugate fibers, said layer of conjugate fibers having a first face and an opposite face, said conjugate fibers being composed of a lower melting component and a higher melting component, wherein a substantial proportion of the surfaces of said fibers comprises said lower melting component, said lower melting component of said conjugate fibers which lie on said first face being fuse bonded to a first layer of a plastic laminated film which comprises said first layer and at least one additional layer, said first layer of said film being thermoplastic and possessing a lower melt temperature than said additional layer of said film, said lower melting component of said fibers having been fuse bonded at a temperature below the melt temperature of said higher melting component of said fibers so that the latter component retains its initial fiber-like integrity;

said process comprising forming an assembly of said laminated film and at least one layer of said conjugate fibers placed adjacent to said first layer of said laminated film;

subjecting said assembly to a temperature sufficient to fuse said lower melting component of said conjugated fibers which lie on said first face as well as the first layer of the film in contact with said fibers without fusing the higher melting component of said conjugate fibers nor the additional layer of the film, while maintaining said assembly under minimal pressure;

and cooling said assembly to resolidify said lower melting component of the fibers as well as its first layer of said film, whereby said fibers are firmly bonded to said film without impairing the integrity of said higher melting component of said fibers.

In accordance with a preferred embodiment of the invention there is provided a process for preparing a water impervious laminated material comprising an inner plastic film sandwiched between two layers of conjugate fibers, each of said layers of conjugate fibers having a first face and an opposite face, said conjugate fibers being composed of a lower melting component and a higher melting component, wherein a substantial proportion of the surface of said fibers comprises said lower melting component, said plastic film comprising a three-layer structure having an inner layer sandwiched between and bonded to two outer layers, said inner layer of said film structure having a melt temperature higher than the melt temperatures of each of said outer layers of said film structure, said lower melting components of both layers of said conjugate fibers which lie on said first faces having been fuse bonded to the adjacent outer layers of said film structure at a temperature below the melt temperature of said higher melting component of said fibers so that the latter component retains its initial fiber-like integrity;

said process comprising forming an assembly of said film sandwiched between two layers of said conjugate fibers, subjecting said assembly to a temperature sufficient to fuse said lower melting components of said conjugate fibers which lie on said first faces in both of said layers thereof as well as both of said outer layers of said film without fusing the higher melting components of said conjugate fibers nor the inner layer of the film, while maintaining the assembly under minimal pressure, and cooling said assembly to resolidify said lower melting components of the fibers as well as the outer layers of the film, whereby said fibers are firmly bonded to said film without impairing the integrity of said higher melting component of said fibers.

The above mentioned fusing step may be carried out by means of a heated embossing calender or by passing the assembly through an oven while said assembly is held between two porous belts under light pressure. Furthermore, the thermal bonding step may also be carried out by any other suitable means for applying localized heat such as by sonic means, lasers, infrared heating or other types of radiant heating.

BRIEF DESCRIPTION OF THE DRAWINGS

FIG. 1 is a schematic side elevation of an apparatus suitable for carring out the process of the invention; and FIG. 2 is a cross-section of the laminated material of the present invention.

Referring first to FIG. 1, one preferred arrangement of an apparatus for carrying out the process of the invention is disclosed. The apparatus shown in FIG. 1 is suitable for making the laminated material of the invention comprising a core of a three-layer film with facings of heat-fusible conjugate fibers on both faces of said core. A web 10 of heat-fusible conjugate fibers is laid down as from a card 12 on an endless belt 14. A laminated three-layer plastic film 20, fed from roller 22, is then laid on top of web 10. The laminated three-layer film 20 may be prepared by known coextrusion means. Film 20, after having been laid upon web 10 forms a double layer web 28.

Web 28 is then passed under another station wherein a second web of heat-fusible conjugate fibers 30 is laid on top as from a card 32. Although webs 10 and 30 are preferably prepared from cards, nevertheless, air-laid webs may also be used although the latter procedure is not particularly suitable in the instance wherein the webs are light weight. Although webs 10 and 30 are preferably fuse bonded in a subsequent step, said webs 10 and 30 may have been initially fuse bonded, in a prior step, before they are laid on either side of the laminated film 20.

After web 30 is laid on top of the double layer web 28, the resulting triple layer web 34 is then passed through a fusion unit 36 to fuse the lower melting component of the conjugate fibers in webs 10 and 30 while maintaining the integrity of the higher melting component of these fibers as fibers, and to fuse or soften the outer surfaces of the laminate film 20 so as to securely bond webs 10 and 30 on either side of laminated film 20. When the multiple layer web emerges from the fusion unit 36, it cools to thereby form the material 38 of the invention. When the material 38 cools, the fused lower melting component of the conjugate fibers, solidifies, and bonds then form where their surfaces touch other fibers. The material 38 is then collected on a conventional wind-up 40. Any suitable means of fusion bonding may be used in fusion unit 36 such as by means of a conventional heated embossing calender, or by passing the assembly through an oven while said assembly is held between two porous belts under light pressure.

FIG. 2 shows a cross-sectional view of the laminated material of the present invention. Thus the laminated plastic film 20 comprising low melting outer layers 13 and 15 and higher melting inner layer 14 are shown sandwiched between layers 10 and 30 of conjugate fibers. The temperature of the fusion unit 36 is maintained below that of the melt temperature of the higher melting component of the conjugate fibers as well as below the melt temperature of inner layer 14 of the laminated film 20. In the instance wherein film 20 consists of a polypropylene core 14 and low melting ethylene/vinyl acetate copolymer layers 13 and 15, sandwiched between two layers of conjugate fibers 10 and 30 comprising a polyethylene/polyethyleneterephthalate sheath/core bi-component fiber, the temperature maintained in the fusion unit (whether the composite is belt or embossed bonded) is preferably in the range of 135° C. to 145° C.

The exact temperatures employed in the fusion unit 36 will depend upon the nature of the conjugate fiber used and the dwell time employed in the fusion unit. For instance when the lower melting component of the conjugate fiber is polyethylene, the bonding temperature is usually from about 110° C. to about 150° C., and when the lower melting component is polypropylene, the bonding temperature is usually from about 150° C. to about 170° C. Dwell times in the fusion unit will usually vary from about 0.01 seconds to about 15 seconds. Specific conditions under which the thermal bonding is achieved are illustrated in the examples below. The temperatures referred to are the temperatures to which the fibers are heated in order to achieve bonding. In order to achieve high speed operations, much higher temperatures with short exposure times can be used.

The examples below illustrate various aspects of the invention.

EXAMPLE 1

A laminated material is prepared by a procedure analogous to that illustrated in FIG. 1 from an inner layer of a tri-component film consisting of one outer layer of ethylene/vinyl acetate copolymer (EVA), a polypropylene core, and the other outer layer being polyethylene. The tri-component film is approximately 1 mil thick. The polyethylene has a softening range of 110°–125° C. and a melting point of about 132° C. The polypropylene has a softening range of 145°–160° C. and a melting point of 165° C. The ethylene/vinyl acetate copolymer has a softening range of 90°–100° C. and a melting point of about 110° C.

A card web (which has already been through-air bonded) and weighing 0.5 ounces per square yard, of high density polyethylene/polyethyleneterephthalate sheath/core bi-component conjugate fiber was placed on each side of the above-mentioned tri-component film. The conjugate fiber had an concentric core and the fiber lengths were about 1.5 inches and the denier was 3. The high density polyethylene sheath had a softening range of 110°–125° C. and a melting point of about 132° C. The polyethyleneterephthalate core has a softening range of 240°–260° C. and a melting point of about 265° C. The polyethylene comprised 50% of the conjugate fiber.

The film and the facings were laminated together using a hot press at about 145° C.

In view of the fact that the two outer surfaces of the tri-component film had different melting temperatures the polyethylene side was placed in contact with the hot plate in order to achieve complete lamination. This resulted in overbonding on the EVA side of the tri-component film so that the resultant laminated material became somewhat stiff.

EXAMPLE 2

A laminated material was made by a procedure analogous to that illustrated in FIG. 1 using a tri-component film consisting of a core of polypropylene sandwiched between two layers of low melting ethylene/vinyl acetate copolymer. The thickness of the film was 1 mil. The polypropylene core had a softening range of 145°–160° C. and a melting point of about 165° C. The ethylene/vinyl acetate copolymer had a softening range of 90°–100° C. and a melting point of about 110° C.

Webs of through-air bonded conjugate fibers (0.5 ounces per square yard bulk) prepared by card webbing were placed on either side of the tri-component film. The conjugate fibers consisted of high density polyethylene/polyethyleneterephthalate sheath/core bi-component fibers, the core being concentric. The high density polyethylene in the conjugate fibers had a softening range of 110°–125° C. and a melting point of about 132° C. The polyethyleneterephthalate core of the conjugate fibers had a softening range of 240°–260° C. and a melting point of about 265° C. The polyethylene comprised 50% of the conjugate fiber.

The conjugate fiber webs were laminated to the tri-component film using a hot press at about 135° C. A minimal compression was applied in order to maintain the bulk of the conjugate fiber facings. The resulting material is a soft, drapable fabric composite which is impervious to water.

EXAMPLE 3

Example 2 is repeated with the following modifications:

Only a two-component film is used, the lower melting component, (namely the ethylene/vinyl acetate copolymer) is placed facing upwardly, with the next layer of polypropylene facing downwardly. Thereafter, only one layer of the high density polyethylene/ polyethyleneterephthalate conjugate fibers is placed on top of the film, with the lower layer of conjugate fibers being omitted. Otherwise, the bonding procedure is the same as that carried out in connection with Example 2. The resultant composite material is a soft drapable fabric.

Certain properties of the material obtained in accordance with Example 2 are as follows:

Thickness of each conjugate fiber facing 20 mil.
Thickness of the tri-component film 1 mil.
Weight of composite material ounces/yard$^2$ 1.5 oz-/yd$^2$.

The material produced in accordance with Example 2 is suitable for use as an operating room drape, a tray cover for surgical instruments, laporatomy packs, obstetric packs, backing layers for diapers or sanitary napkins and for any other applications wherein an absorbent impermeable material would be desirable.

The material produced in accordance with Example 2 possesses improved integrity, durability, and strength as well as good absorptive capacity with respect to the facing layers. Furthermore, in view of the fact that the high melting component of the conjugate fibers of the facing layers retain their fiber-like integrity, the bonding strength of the layers of conjugate fibers to the plastic film is much greater than would be the case if non-conjugate filaments only were to be used for the nonwoven facing layers which are bonded to the water impermeable film. Another advantage of the use of the conjugate fibers of the present invention is as follows: Pinholing of the film due to the high pressure and temperature used is negated.

I claim:

1. A water impervious laminated material comprising at least one layer of conjugate fibers, said layer of conjugate fibers having a first face and an opposite face, said conjugate fibers being composed of a lower melting component and a higher melting component, wherein a substantial proportion of the surfaces of said fibers comprises said lower melting component, said lower melting component of said conjugate fibers which lie on said first face being fuse bonded to a first layer of a plastic laminated film which comprises said first layer and at least one additional layer of plastic, said first layer of said film being thermoplastic and possessing a lower melt temperature than said additional layer of said film, said lower melting component of said fibers having been fuse bonded at a temperature below the melt temperature of said higher melting component of said fibers and said additional layer of plastic whereby the latter component retains its initial fiber-like integrity and said additional layer of plastic remains unfused and free of any perforations.

2. The material of claim 1, in which the melt temperature of the lower melting component of the conjugate fibers is no more than 35° C. higher or lower than the melt temperature of the first layer of the thermoplastic film.

3. The material of claim 1, wherein the conjugate fiber is a polyethylene/polyester sheath/core bi-component fiber.

4. The material of claim 1, in which the first layer of the film is selected from the group consisting of ethylene/vinyl acetate copolymer, polyethylene, chlorinated polyethylene and polyvinyl chloride and the additional layer of the film comprises isotactic polypropylene.

5. The material of claim 1 in which said layer of conjugate fibers is blended with non-conjugate fusible fibers, with the proviso that said first face of said layer of conjugate fibers contains a plurality of conjugate fibers in said blend.

* * * * *